United States Patent
Allum et al.

(10) Patent No.: US 8,888,711 B2
(45) Date of Patent: Nov. 18, 2014

(54) FLOW SENSOR

(75) Inventors: Todd W. Allum, Redlands, CA (US); Malcolm R. Williams, San Clemente, CA (US); Joseph Cipollone, Moreno Valley, CA (US)

(73) Assignee: Carefusion 203, Inc., San Diego, CA (US)

(*) Notice: Subject to any disclaimer, the term of this patent is extended or adjusted under 35 U.S.C. 154(b) by 1052 days.

(21) Appl. No.: 12/099,588

(22) Filed: Apr. 8, 2008

(65) Prior Publication Data
US 2009/0250059 A1 Oct. 8, 2009

(51) Int. Cl.
| | |
|---|---|
| A61B 5/08 | (2006.01) |
| G01F 1/36 | (2006.01) |
| G01F 1/40 | (2006.01) |
| G01F 15/00 | (2006.01) |
| G01F 1/50 | (2006.01) |
| A61M 16/00 | (2006.01) |

(52) U.S. Cl.
CPC .. *G01F 1/36* (2013.01); *G01F 1/40* (2013.01); *G01F 15/00* (2013.01); *A61M 2205/42* (2013.01); *G01F 1/50* (2013.01); *A61M 2016/0021* (2013.01); *A61M 2016/0027* (2013.01); *A61M 16/0051* (2013.01); *A61M 2016/0036* (2013.01)
USPC ........ 600/538; 600/540; 600/543; 73/861.52; 73/861.42

(58) Field of Classification Search
CPC ....... G01F 1/40; G01F 1/6842; A61B 5/0871; A61B 5/087; A61B 5/097; A61B 5/095; A61B 5/093
USPC .................. 600/538–543; 73/861.02–861.03, 73/861.29, 204.21, 861.42, 861.52, 73/861.63, 861.55, 861.58, 861.61, 73/861.57, 861.22; 128/204.23; 138/40, 138/44
See application file for complete search history.

(56) References Cited

U.S. PATENT DOCUMENTS

| | | | |
|---|---|---|---|
| 56,614 | A | 7/1866 | Roots et al. |
| 587,907 | A | 8/1897 | Ames et al. |

(Continued)

FOREIGN PATENT DOCUMENTS

| | | |
|---|---|---|
| EP | 0239026 | 9/1987 |
| EP | 0521709 | 1/1993 |

(Continued)

OTHER PUBLICATIONS

M.L. Munjal, "Acoustics of Ducts and Mufflers," John Wiley & Sons, 1987, chapter 8.

(Continued)

*Primary Examiner* — Michael Kahelin
*Assistant Examiner* — Tho Tran
(74) *Attorney, Agent, or Firm* — McDermott Will & Emery LLP

(57) ABSTRACT

A bi-directional flow sensor is adapted for reducing pneumatic noise during pressure sensing with a flow passing through the flow sensor. The flow sensor comprises a hollow, tubular member having a throat section disposed between a ventilator end and a patient end. A flow restrictor is disposed in the throat section and is adapted to measure differential pressure in the flow. A baffle is mounted at the ventilator end and is adapted to minimize non-axial flow at pressure taps located on opposing ends of the flow restrictor. The patient end includes a flow obstruction configured to promote uniform velocity across the flow at the pressure taps during exhalation flow from the patient end to the ventilator end. The flow sensor minimizes pneumatic noise to less than 0.1 LPM to allow accurate patient flow measurement and triggering of inhalation and exhalation phases at flow rates of 0.2 LPM.

18 Claims, 3 Drawing Sheets

(56) References Cited

U.S. PATENT DOCUMENTS

| | | | |
|---|---|---|---|
| 1,769,153 A | 7/1930 | Meyer | |
| 2,014,932 A | 9/1935 | Hallett | 230/141 |
| 2,787,999 A | 4/1957 | Bennett | 128/30 |
| 3,089,638 A | 5/1963 | Rose | 230/141 |
| 3,094,274 A | 6/1963 | Thompson | 230/224 |
| 3,196,680 A * | 7/1965 | Curran | 73/861.52 |
| 3,371,856 A | 3/1968 | Thelen et al. | 230/141 |
| 3,459,395 A | 8/1969 | Scotto | 248/20 |
| 3,658,443 A | 4/1972 | Fumagalli | 417/384 |
| 3,941,206 A | 3/1976 | Halter | 181/50 |
| 4,080,103 A | 3/1978 | Bird | 417/3 |
| 4,121,578 A | 10/1978 | Torzala | 128/142 R |
| 4,215,977 A | 8/1980 | Weatherston | 418/1 |
| 4,220,219 A | 9/1980 | Flugger | 181/265 |
| 4,227,869 A | 10/1980 | Eriksson | 418/206 |
| 4,239,039 A | 12/1980 | Thompson | 128/205.24 |
| 4,267,899 A | 5/1981 | Wagner et al. | 181/272 |
| 4,323,064 A | 4/1982 | Hoenig et al. | 128/204.21 |
| 4,448,192 A | 5/1984 | Stawitcke et al. | 128/204.26 |
| 4,455,132 A | 6/1984 | Messori | 418/206 |
| 4,495,947 A | 1/1985 | Motycka | 128/205.14 |
| 4,564,345 A | 1/1986 | Mueller | 418/206 |
| 4,595,349 A | 6/1986 | Preston et al. | 418/206 |
| 4,609,335 A | 9/1986 | Uthoff, Jr. | 418/201 |
| 4,638,672 A * | 1/1987 | McCall | 73/861.52 |
| 4,662,912 A * | 5/1987 | Perkins | 96/140 |
| 4,666,384 A | 5/1987 | Kaga et al. | 418/150 |
| 4,673,058 A | 6/1987 | Roberts et al. | 181/266 |
| 4,684,330 A | 8/1987 | Andersson et al. | 417/360 |
| 4,686,999 A | 8/1987 | Snyder et al. | 128/716 |
| 4,702,240 A | 10/1987 | Choui | 128/204.18 |
| 4,768,934 A | 9/1988 | Soeters, Jr. | 418/1 |
| 4,781,541 A | 11/1988 | Sohler et al. | 417/312 |
| 4,794,922 A | 1/1989 | DeVries | 128/204.18 |
| 4,844,044 A | 7/1989 | McGovern | 123/559.1 |
| 4,846,302 A | 7/1989 | Hetherington | 181/243 |
| 4,867,151 A | 9/1989 | Bird | 128/201.17 |
| 4,938,670 A | 7/1990 | Lee | 418/150 |
| 4,957,107 A | 9/1990 | Sipin | 128/204.21 |
| 4,975,032 A | 12/1990 | Arai et al. | 418/150 |
| 5,040,959 A | 8/1991 | Fukagawa | 418/150 |
| 5,056,995 A | 10/1991 | Tamura et al. | 418/201.1 |
| 5,131,829 A | 7/1992 | Hampton | 418/189 |
| 5,145,349 A | 9/1992 | McBurnett | 418/206 |
| 5,152,684 A | 10/1992 | Steffens | 418/150 |
| 5,161,525 A | 11/1992 | Kimm et al. | 128/204.26 |
| 5,211,170 A | 5/1993 | Press | 128/204.18 |
| 5,222,148 A | 6/1993 | Yuan | 381/71 |
| 5,237,987 A | 8/1993 | Anderson et al. | 128/204.18 |
| 5,239,994 A | 8/1993 | Atkins | 128/204.18 |
| 5,335,651 A | 8/1994 | Foster et al. | 128/202.13 |
| 5,350,888 A | 9/1994 | Sager, Jr. et al. | 181/247 |
| 5,379,650 A * | 1/1995 | Kofoed et al. | 73/861.52 |
| 5,398,676 A | 3/1995 | Press et al. | 128/204.23 |
| 5,439,358 A | 8/1995 | Weinbrecht | 418/15 |
| 5,452,714 A | 9/1995 | Anderson et al. | 128/205.11 |
| 5,542,416 A | 8/1996 | Chalvignac | 128/204.23 |
| 5,577,152 A | 11/1996 | Chen | 388/804 |
| 5,582,163 A | 12/1996 | Bonassa | 128/204.26 |
| 5,632,270 A | 5/1997 | O'Mahony et al. | 128/204.24 |
| 5,638,600 A | 6/1997 | Rao et al. | 29/888.02 |
| 5,664,563 A | 9/1997 | Schroeder et al. | 128/204.25 |
| 5,687,717 A | 11/1997 | Halpern et al. | 128/630 |
| 5,694,926 A | 12/1997 | DeVries et al. | 128/205.24 |
| 5,701,883 A | 12/1997 | Hete et al. | 128/204.26 |
| 5,702,240 A | 12/1997 | O'Neal et al. | 418/9 |
| 5,760,348 A | 6/1998 | Heuser | 181/272 |
| 5,763,792 A | 6/1998 | Kullik | 73/861.53 |
| 5,783,782 A | 7/1998 | Sterrett et al. | 181/272 |
| 5,823,186 A | 10/1998 | Rossen et al. | 128/204.21 |
| 5,831,223 A | 11/1998 | Kesselring | 181/227 |
| 5,868,133 A | 2/1999 | DeVries et al. | 128/204.21 |
| 5,881,722 A | 3/1999 | DeVries et al. | 128/204.21 |
| 5,918,597 A | 7/1999 | Jones et al. | 128/205.18 |
| 5,931,159 A | 8/1999 | Suzuki et al. | 128/204.18 |
| 5,944,501 A | 8/1999 | Yokoi | 418/181 |
| 6,009,871 A | 1/2000 | Kiske et al. | 128/204.21 |
| 6,076,523 A | 6/2000 | Jones et al. | 128/205.11 |
| 6,099,277 A | 8/2000 | Patel et al. | 418/1 |
| 6,102,038 A | 8/2000 | DeVries | 128/205.24 |
| 6,125,844 A | 10/2000 | Samiotes | 128/200.23 |
| 6,152,129 A | 11/2000 | Berthon-Jones | 128/200.24 |
| 6,152,135 A | 11/2000 | DeVries et al. | 128/205.24 |
| 6,155,257 A | 12/2000 | Lurie et al. | 128/204.23 |
| 6,158,430 A | 12/2000 | Pfieffer et al. | 128/202.27 |
| 6,158,434 A | 12/2000 | Lugtigheid et al. | 128/204.22 |
| 6,164,412 A | 12/2000 | Allman | 181/272 |
| 6,176,693 B1 | 1/2001 | Conti | 418/180 |
| 6,279,574 B1 | 8/2001 | Richardson et al. | 128/204.18 |
| 6,283,246 B1 | 9/2001 | Nishikawa | 181/255 |
| 6,305,372 B1 | 10/2001 | Servidio | 128/204.21 |
| 6,354,558 B1 | 3/2002 | Li | 248/615 |
| 6,412,483 B1 | 7/2002 | Jones et al. | 128/205.11 |
| 6,474,960 B1 | 11/2002 | Hansmann | 417/363 |
| 6,484,719 B1 | 11/2002 | Berthon-Jones | 128/204.23 |
| 6,526,970 B2 | 3/2003 | DeVries et al. | 128/204.21 |
| 6,543,449 B1 | 4/2003 | Woodring et al. | 128/204.18 |
| 6,558,137 B2 | 5/2003 | Tomell et al. | 417/312 |
| 6,564,798 B1 | 5/2003 | Jalde | 128/205.24 |
| 6,571,792 B1 | 6/2003 | Hendrickson et al. | 128/203.12 |
| 6,571,796 B2 | 6/2003 | Banner et al. | 128/204.26 |
| 6,591,835 B1 | 7/2003 | Blanch | 128/204.25 |
| 6,615,831 B1 | 9/2003 | Tuitt et al. | 128/204.18 |
| 6,619,286 B2 | 9/2003 | Patel | 128/204.26 |
| 6,626,175 B2 | 9/2003 | Jafari et al. | 128/204.21 |
| 6,629,525 B2 | 10/2003 | Hill et al. | 128/202.26 |
| 6,629,531 B2 | 10/2003 | Gleason et al. | 128/205.25 |
| 6,629,934 B2 | 10/2003 | Mault et al. | 600/538 |
| 6,631,716 B1 | 10/2003 | Robinson et al. | 128/204.21 |
| 6,637,430 B1 | 10/2003 | Voges et al. | 128/200.14 |
| 6,651,658 B1 | 11/2003 | Hill et al. | 128/204.23 |
| 6,666,209 B2 | 12/2003 | Bennett et al. | 128/200.24 |
| 6,672,300 B1 | 1/2004 | Grant | 124/204.26 |
| 6,691,702 B2 | 2/2004 | Appel et al. | 128/202.26 |
| 6,691,707 B1 | 2/2004 | Gunaratnam et al. | 128/206.21 |
| 6,708,690 B1 | 3/2004 | Hete et al. | 128/204.18 |
| 6,742,399 B2 * | 6/2004 | Kunz et al. | 73/861.52 |
| 6,745,770 B2 | 6/2004 | McAuliffe et al. | 128/205.24 |
| 6,752,240 B1 | 6/2004 | Schlagenhaft | 181/249 |
| 6,764,534 B2 | 7/2004 | McCombs et al. | 96/111 |
| 6,770,037 B2 | 8/2004 | Sullivan et al. | 600/529 |
| 6,782,888 B1 | 8/2004 | Friberg et al. | 128/204.18 |
| 6,802,225 B2 | 10/2004 | Shahar et al. | 73/861.52 |
| 6,820,618 B2 | 11/2004 | Banner et al. | 128/204.23 |
| 6,837,260 B1 | 1/2005 | Kuehn | 137/315.01 |
| 6,877,511 B2 | 4/2005 | DeVries et al. | 128/204.26 |
| 6,968,842 B1 | 11/2005 | Truschel et al. | 128/204.18 |
| 7,004,908 B2 | 2/2006 | Sullivan et al. | 600/529 |
| 7,011,092 B2 | 3/2006 | McCombs et al. | 128/205.12 |
| 7,032,589 B2 | 4/2006 | Kerechanin et al. | 128/200.24 |
| 7,063,084 B2 | 6/2006 | McDonald | 128/200.28 |
| 7,066,178 B2 | 6/2006 | Gunaratnam et al. | 128/206.21 |
| 7,066,985 B2 | 6/2006 | Deane et al. | 95/96 |
| 7,073,499 B1 | 7/2006 | Reinhold et al. | 128/200.18 |
| 7,086,366 B1 | 8/2006 | Killion | 123/192.2 |
| 7,118,536 B2 | 10/2006 | Haberland et al. | 600/538 |
| 7,121,276 B2 | 10/2006 | Jagger et al. | 128/201.21 |
| 7,168,429 B2 | 1/2007 | Matthews et al. | 128/204.21 |
| 7,171,963 B2 | 2/2007 | Jagger et al. | 128/201.21 |
| 7,183,681 B2 | 2/2007 | Segawa et al. | 310/68 B |
| 7,188,621 B2 | 3/2007 | DeVries et al. | 128/204.21 |
| 7,225,809 B1 | 6/2007 | Bowen et al. | 128/204.21 |
| 7,226,280 B1 | 6/2007 | Yokoi | 418/206.4 |
| 7,329,304 B2 | 2/2008 | Bliss et al. | 95/12 |
| 7,331,342 B2 | 2/2008 | Spearman et al. | 128/203.14 |
| 7,335,243 B2 | 2/2008 | Homan et al. | 55/385.2 |
| 7,351,034 B2 | 4/2008 | Cens et al. | 416/61 |
| 7,368,005 B2 | 5/2008 | Bliss et al. | 96/121 |
| 2001/0044588 A1 | 11/2001 | Mault | 600/549 |
| 2002/0134378 A1 | 9/2002 | Finnegan et al. | 128/200.24 |
| 2003/0057904 A1 | 3/2003 | Sacher | 318/268 |
| 2003/0122100 A1 * | 7/2003 | Baumann | 251/305 |
| 2003/0208113 A1 | 11/2003 | Mault et al. | 600/316 |
| 2004/0074495 A1 | 4/2004 | Wickham et al. | 128/204.18 |

(56) References Cited

U.S. PATENT DOCUMENTS

| | | | |
|---|---|---|---|
| 2004/0147818 A1 | 7/2004 | Levy et al. | 600/300 |
| 2004/0211422 A1 | 10/2004 | Arcilla et al. | 128/204.19 |
| 2004/0221854 A1 | 11/2004 | Hete et al. | 128/207.16 |
| 2004/0226562 A1 | 11/2004 | Bordewick | 128/204.23 |
| 2005/0017019 A1* | 1/2005 | Richter | 222/1 |
| 2005/0112013 A1 | 5/2005 | DeVries et al. | 418/206.1 |
| 2005/0124866 A1 | 6/2005 | Elaz et al. | 600/301 |
| 2005/0166921 A1 | 8/2005 | DeVries et al. | 128/204.21 |
| 2005/0188991 A1 | 9/2005 | Sun et al. | 128/204.23 |
| 2005/0202776 A1* | 9/2005 | Avedon | 454/230 |
| 2005/0241642 A1 | 11/2005 | Krzysztofik | 128/206.15 |
| 2006/0053902 A1* | 3/2006 | Good et al. | 73/861.52 |
| 2006/0065672 A1 | 3/2006 | LeCourt et al. | 222/3 |
| 2006/0069326 A1 | 3/2006 | Heath | 601/41 |
| 2006/0070624 A1 | 4/2006 | Kane et al. | 128/204.23 |
| 2006/0124128 A1 | 6/2006 | Deane et al. | 128/204.21 |
| 2006/0144396 A1 | 7/2006 | DeVries et al. | 128/204.21 |
| 2006/0144399 A1 | 7/2006 | Davidowski et al. | 128/205.21 |
| 2006/0144405 A1 | 7/2006 | Gunaratnam et al. | 128/206.21 |
| 2006/0150973 A1 | 7/2006 | Chalvignac | 128/214.21 |
| 2006/0174871 A1 | 8/2006 | Jagger et al. | 128/201.21 |
| 2006/0174872 A1 | 8/2006 | Jagger et al. | 128/201.21 |
| 2006/0174874 A1 | 8/2006 | Jagger et al. | 128/201.21 |
| 2006/0174875 A1 | 8/2006 | Jagger et al. | 128/201.21 |
| 2006/0174877 A1 | 8/2006 | Jagger et al. | 128/201.21 |
| 2006/0174878 A1 | 8/2006 | Jagger et al. | 128/201.21 |
| 2006/0174880 A1 | 8/2006 | Jagger et al. | 128/201.25 |
| 2006/0174881 A1 | 8/2006 | Jagger et al. | 128/201.25 |
| 2006/0174882 A1 | 8/2006 | Jagger et al. | 128/201.25 |
| 2006/0201503 A1 | 9/2006 | Breen | 128/204.18 |
| 2006/0213518 A1 | 9/2006 | DeVries et al. | 128/204.21 |
| 2006/0249149 A1 | 11/2006 | Meier et al. | 128/204.18 |
| 2006/0266355 A1 | 11/2006 | Misholi | 128/204.23 |
| 2006/0283450 A1 | 12/2006 | Shissler et al. | 128/204.21 |
| 2007/0044799 A1 | 3/2007 | Hete et al. | 128/205.11 |
| 2007/0062529 A1 | 3/2007 | Choncholas et al. | 128/204.22 |
| 2007/0062532 A1 | 3/2007 | Choncholas | 128/204.23 |
| 2007/0068526 A1 | 3/2007 | Lang et al. | 128/204.22 |
| 2007/0079826 A1 | 4/2007 | Kramer et al. | 128/200.14 |
| 2007/0113843 A1 | 5/2007 | Hughes | 128/200.24 |
| 2007/0113849 A1 | 5/2007 | Matthews et al. | 128/204.22 |
| 2007/0169776 A1 | 7/2007 | Kepler et al. | 128/200.23 |
| 2007/0181127 A1 | 8/2007 | Jin et al. | 128/204.21 |
| 2007/0193580 A1 | 8/2007 | Feldhahn et al. | 128/204.18 |
| 2007/0215146 A1 | 9/2007 | Douglas et al. | 128/200.24 |
| 2007/0221224 A1 | 9/2007 | Pittman et al. | 128/204.22 |
| 2007/0235030 A1 | 10/2007 | Teetzel et al. | 128/205.12 |
| 2007/0265877 A1 | 11/2007 | Rice et al. | 705/2 |
| 2007/0277825 A1 | 12/2007 | Bordewick et al. | 128/204.23 |
| 2008/0000474 A1 | 1/2008 | Jochle et al. | 128/204.18 |
| 2008/0029096 A1 | 2/2008 | Kollmeyer et al. | 128/204.21 |
| 2008/0035149 A1 | 2/2008 | Sutton | 128/205.24 |
| 2008/0039701 A1 | 2/2008 | Ali et al. | 600/301 |
| 2008/0066739 A1 | 3/2008 | LeMahieu et al. | 128/200.14 |
| 2008/0078395 A1 | 4/2008 | Ho et al. | 128/205.24 |
| 2008/0099017 A1 | 5/2008 | Bordewick et al. | 128/204.21 |
| 2008/0110455 A1 | 5/2008 | Dunsmore et al. | 128/200.24 |
| 2008/0110458 A1 | 5/2008 | Srinivasan et al. | 128/203.26 |
| 2008/0110462 A1 | 5/2008 | Chekal et al. | 128/204.26 |
| 2008/0127976 A1 | 6/2008 | Acker et al. | 128/204.18 |
| 2008/0214948 A1* | 9/2008 | Myklebust et al. | 600/538 |
| 2009/0137920 A1* | 5/2009 | Colman et al. | 600/543 |
| 2010/0309445 A1* | 12/2010 | Schultz | 355/30 |

FOREIGN PATENT DOCUMENTS

| | | |
|---|---|---|
| EP | 0938909 | 9/1999 |
| EP | 1130761 | 9/2001 |
| GB | 2157370 | 10/1985 |
| JP | H09-502025 A | 2/1997 |
| JP | 2002-515297 A | 5/2002 |
| JP | 3615371 B2 | 2/2005 |
| WO | WO 89/10768 | 11/1989 |
| WO | WO 92/11054 | 7/1992 |
| WO | WO 96/11717 | 4/1996 |
| WO | WO 97/11522 | 3/1997 |
| WO | WO 97/15343 | 5/1997 |
| WO | WO 99/64825 | 12/1999 |
| WO | WO 00/45883 | 8/2000 |
| WO | WO 02/11861 | 2/2002 |
| WO | WO 2004/040745 | 5/2004 |

OTHER PUBLICATIONS

Eaton, "Why an Eaton Supercharger?" www.eaton.com/supercharger/whysuper.html.
Chinese Fourth Office Action, Chinese Application No. 200910130396.0, dated May 13, 2013, pp. 1-3.
Japanese Office Action, Japanese Application No. 2009-089852, dispatch date Aug. 20, 2013, pp. 1-5.

* cited by examiner

FLOW SENSOR

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates generally to patient ventilation systems and, more particularly, to a bi-directional flow sensor having improved accuracy in measuring respiratory flow to and from a patient.

Mechanical ventilators are used to provide respiratory support to a patient by assisting in the inhalation and exhalation phases of the breathing cycle. In one arrangement, the mechanical ventilator may be connected to the patient by a wye fitting. The wye fitting is, in turn, fluidly connected to the patient's airway by a patient tube connected to a patient interface. The wye fitting may have an exhalation valve connected to one leg of the wye fitting.

The exhalation valve is moved between open and closed positions according to the phase of the breathing cycle. During the inspiration phase, the exhalation valve is closed to allow compressed gas from the ventilator to be delivered to the patient. During the exhalation phase, the exhalation valve opens to allow the patient to exhale to atmosphere. In certain ventilator arrangements, a positive end expiratory pressure (PEEP) valve is used in combination with the exhalation valve in order to provide an elevated back-pressure above atmosphere during the exhalation phase.

A flow sensor is used to determine the flow rate of compressed gas passing from the ventilator to the patient as well as determine the flow rate of exhalation gas flowing from the patient to the exhalation valve. Differential pressure detection is one of the more common techniques for measuring flow of a gas. Differential pressure flow sensors include a flow restrictor positioned within the flow of gas passing through the sensor to allow measurement of the pressure drop (i.e., the differential pressure) that occurs across the flow restrictor. Bi-directional flow sensors are capable of determining flow rate in either direction as a function of the measurable pressure difference between upstream and downstream pressure taps on opposite ends of the flow restrictor. The measurable pressure difference is correlated to an empirically-established flow rate.

In some cases, the patient interface is provided as an endotracheal tube for delivering pressurized gas from the mechanical ventilator to the patient. The endotracheal tube is typically of a relatively small diameter. An airway adapter is used to mate the small diameter endotracheal tube to the larger diameter flow sensor fitting which is available in standard sizes. The flow sensor is preferably located as close to the patient as possible and, in some prior art arrangements, the flow sensor may be incorporated into the wye fitting or may be located between the wye fitting and the patient interface.

Because of the size discrepancy between the relatively small diameter endotracheal tube and the larger diameter flow sensor, exhalation by the patient results in a relatively high velocity pressure jet exiting the endotracheal tube and entering the flow sensor. The artificially high velocity pressure from the endotracheal tube impinges on the pressure taps of the flow restrictor in the flow sensor. This high velocity pressure jet results in an artificially high differential pressure measurement for the given flow relative to the empirically-established flow rate/differential pressure relationship. The result is an artificially high flow rate measurement.

In an attempt to overcome the problem of an artificially high flow velocity generated by the pressure jet, some prior art ventilation systems increase the distance from the endotracheal tube to the flow sensor by approximately six inches. This increased distance between the flow sensor and the endotracheal tube permits the pressure jet to more uniformly disperse within the flow sensor prior to impinging upon the pressure taps. In this manner, the flow velocity is relatively constant across the cross-sectional area of the flow sensor such that pressure measurements are believed to be more accurate. Unfortunately, the increase in distance from the flow sensor to the endotracheal tube also increases the amount of re-breathed volume or deadspace in the patient's airway. The increased deadspace results in re-breathing of previously exhaled gasses.

Another problem associated with flow measurement is that during the inhalation phase, inaccurate pressure measurements at the flow sensor can occur as a result of pneumatic noise in the flow. Such pneumatic noise may include turbulence, vibrations, or asymmetric flow conditions at the ventilator end of the flow sensor (i.e., opposite the patient end). Certain mechanical ventilation systems are configured to operate with a bias flow which may include pneumatic noise. For example, the mechanical ventilator system similar to that disclosed in U.S. Pat. No. 6,102,038 issued to DeVries operates with a bias flow which circulates through the wye fitting depending on whether the exhalation valve is open or closed.

For most applications, the bias flow is typically in the range of about 2-10 liters per minute (LPM) and can introduce pneumatic noise at the flow sensor which reduces the accuracy of the flow sensor. The pneumatic noise in the bias flow may be the product of asymmetric flow conditions at the inlet to the flow sensor. More specifically, because of the geometry of the wye fitting, the bias flow may enter the flow sensor in a non-axial direction creating a flow vortex or cross flow at the flow sensor which results in inaccurate pressure measurement at the pressure taps of the flow sensor.

Pressure sensed in the flow sensor can be used to cycle the mechanical ventilator exhalation valve according to patient-initiated inspiration and exhalation phases of each breathing cycle. Particularly for neonatal and pediatric patients, it is desirable to minimize pneumatic noise in the bias flow such that the 0.2 LPM flow rate at which the inspiration and exhalation phases are triggered, is not disturbed by the pneumatic noise. In this regard, it is desirable that such pneumatic noise is maintained at or below 0.1 LPM.

As can be seen, there exists a need in the art for a flow sensor that is adapted for use with neonatal and pediatric patients. More specifically, there exists a need in the art for a flow sensor that can operate with reduced pneumatic noise such that patient-initiated inspiration and exhalation phases of each breathing cycle are triggered at the appropriate flow rate. Additionally, there exists a need in the art for a flow sensor that is adaptable for use with small diameter endotracheal tubes.

Preferably, the flow sensor is configured to eliminate the artificially-high pressure measurement produced by the pressure jet discharged from the endotracheal tubes during exhalation. Furthermore, it is desirable that the flow sensor is configured to minimize deadspace in order to prevent $CO_2$ re-breathing by the patient. Finally, there exists a need in the art for a flow sensor which overcomes the adverse effects of pneumatic noise at the ventilator end while minimizing resistance to airflow during inspiration and exhalation.

BRIEF SUMMARY

The above-described needs associated with flow sensors for mechanical ventilators is specifically addressed by the present invention which provides a bi-directional flow sensor. The flow sensor is adapted for use with a mechanical ventilator for measuring a flow of compressed gas to a patient during inhalation and exhalation. The mechanical ventilator may be connected to the patient by means of a conventional wye fitting. The wye fitting may also be fluidly connected to an exhalation valve and/or positive end expiratory pressure (PEEP) valve. The flow sensor is specifically adapted to limit pneumatic noise to about 0.1 liters per minute (LPM) such that triggering of patient-inspired inspiration and exhalation can occur at about 0.2 LPM. The flow sensor may be integrated into the wye fitting or provided as a separate component to the wye fitting. The flow sensor may be connected to a patient tube which, in turn, may be connected to a patient interface such as an endotracheal tube.

In its broadest sense, the flow sensor comprises an elongated, hollow tubular member having a flow restrictor for measuring pressure differential. The flow sensor may include a baffle at one end of the tubular member and/or a flow obstruction at an opposite end of the tubular member. The baffle is specifically adapted to straighten non-axial flow such as that which characterizes bias flow from the mechanical ventilator. The flow obstruction is preferably axial aligned with the endotracheal tube such that the pressure jet exiting the endotracheal tube during patient exhalation is dispersed into a uniform velocity profile prior to reaching the flow restrictor wherein the exhalation flow is measured.

The tubular member includes a ventilator end connected to the mechanical ventilator and a patient end connected to the patient airway. The tubular member may be fitted with a conventional airway adapter having the endotracheal tube connected thereto. The tubular member may be cylindrically-shaped with a bore defining an interior surface and having a central axis. The bore may have a reduced cross sectional area at a throat section located between the ventilator end and the patient end. The throat section constricts the exhaled flow entering the patient end prior to the flow reaching the flow restrictor wherein the exhaled flow is measured.

The flow restrictor is diametrically disposed within the throat section such that the flow restrictor bisects the throat section. In this regard, the flow restrictor is mounted transversely relative to the central axis. The flow restrictor includes a pair of pressure taps disposed on axially opposed ends thereof. Each one of the pressure taps defines a tap height which is preferably symmetrically disposed about the central axis. Each of the pressure taps is fluidly connected by separate fluid passageways to a corresponding pair of exterior pressure ports.

The pressure ports may be fluidly connected, such as via pressure tubes or fittings, to a pressure transducer to allow conversion of pressure differential to flow rate. The sensed pressure is used to measure inspired/expired gas flow. The flow restrictor preferably has a symmetrical aerodynamic cross sectional shape with an aspect ratio that is aligned with the central axis.

The baffle is disposed within the bore at the ventilator end and comprises a plurality of vanes which extend radially outwardly from the central axis and which are axially aligned with the central axis. The baffle is preferably sized and configured to minimize non-axial flow at the pressure taps. In this regard, the baffle is configured to straighten the angular nature of the bias flow entering the flow sensor. The bias flow is straightened by the vanes prior to reaching the flow restrictor wherein pressure differential in the flow is measured and thereafter converted to flow rate. In this regard, the baffle prevents cross flow at the flow restrictor in order to increase the accuracy of pressure measurement.

Each one of the vanes preferably includes a notch formed on a radially inward side (i.e., adjacent the central axis) of the baffle at an end thereof opposite the ventilator end. The notches in the vanes collectively define a common pressure relief for the baffle. The pressure relief is specifically adapted to minimize pressure differential between adjacent vane passages (i.e., vane-to-vane pressure differential). In this manner, the flow from the ventilator end is preferably of a uniform velocity profile to ensure accuracy of pressure measurement at the flow restrictor.

On an opposite end of the flow sensor, a flow obstruction is disposed within the bore between the patient end and the throat section. The flow obstruction is preferably mounted transversely relative to the central axis such that the flow obstruction bisects the bore (i.e., is diametrically disposed therewithin). In addition, the flow obstruction is preferably oriented orthogonally or perpendicularly relative to the flow restrictor when viewed from an axial direction.

Furthermore, the flow obstruction preferably has an aerodynamic cross sectional shape such as a diamond shape or a teardrop shape. The flow obstruction is preferably configured to promote uniform velocity across the bore at the throat section in order to improve the accuracy of pressure measurement at the pressure taps. The flow obstruction preferably has an obstruction height that prevents direct impingement of the high velocity pressure jet from the endotracheal tube upon the pressure taps which may result in erroneous differential pressure measurements.

The flow sensor is specifically adapted for use with a mechanical ventilator and is preferably configured such that pneumatic noise is maintained at less than 0.1 liters per minute (LPM) in order to allow triggering of patient-inspired inhalation and exhalation phases of a breathing cycle at a relatively small flow rate of 0.2 LPM as may be required in neonatal ventilation.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
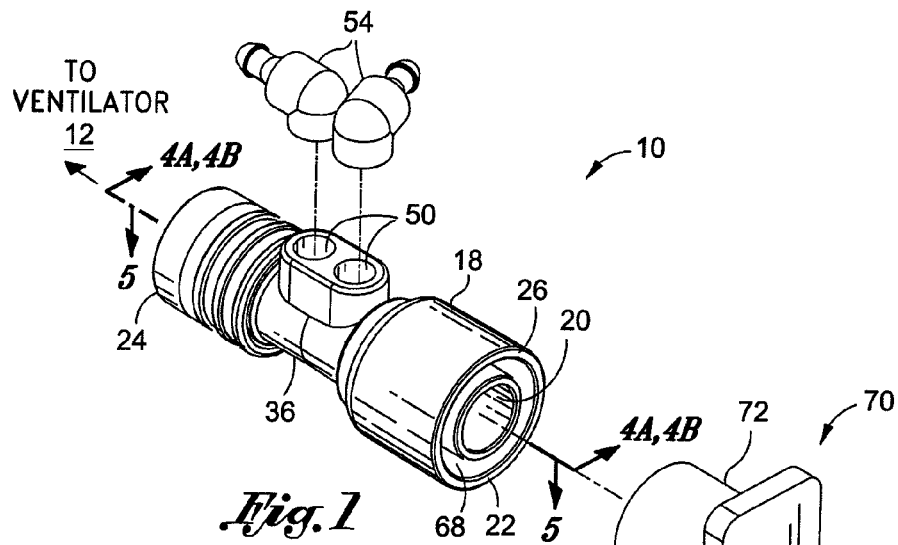
FIG. 1 is an exploded perspective view of a flow sensor of the present invention and further illustrating an airway adapter fluidly connecting to an endotracheal tube.
Figure 2:
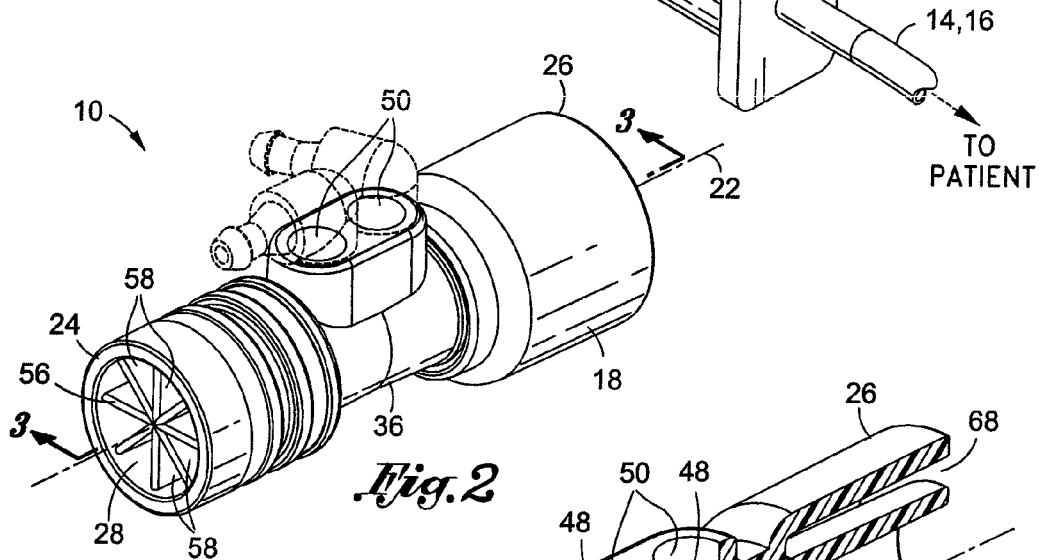
FIG. 2 is a perspective view of the flow sensor taken from a patient end thereof.

Referring now to the drawings wherein the showings are for purposes of illustrating preferred embodiments of the present invention and not for purposes of limiting the same, shown in FIGS. 1 and 2 is a perspective view of a bi-directional flow sensor 10 specifically adapted for sensing pressure within a flow passing through the flow sensor 10. The flow sensor 10 is shown as being adapted to be interconnected to a patient tube 14 such as an endotracheal tube 16 which may have a relatively small size (i.e., small inner diameter 76). The adapter 70 is frictionally engageable to the flow sensor 10 such as by insertion of the adapter 70 into an annular groove 68 formed on one end of the flow sensor 10.

The endotracheal tube 16 may also have a relatively large diameter for use with adults. Alternative configurations of the patient tube 14 may be used with the flow sensor other than endotracheal tubes. Regardless of their specific configuration, the patient tube 14 is adapted to connect the patient airway to the flow sensor 10. The flow sensor 10 is adapted to facilitate accurate measurement of flow rates passing therethrough regardless of the patient tube 14 configuration.

The flow sensor 10 includes a flow obstruction 64 at the patient end 26. At each end of the flow obstruction 64 are a pair of pressure taps 44b a, 44b. The flow obstruction 64 is specifically oriented to be in direct alignment with a high velocity pressure jet discharged from the endotracheal tube 16 during exhalation. In this regard, the flow obstruction 64 is specifically adapted to disperse the pressure jet and promote a generally uniform velocity across the relatively larger cross sectional area of the flow sensor 10 at the patient end 26 pressure tap 44b. In this manner, the flow obstruction 64 facilitates accurate measurement of exhalation flow.

Referring particularly to FIG. 1, the flow sensor 10 may include a pair of fittings 54 sized and configured to engage a corresponding pair of pressure tube connector 52 openings formed on an exterior side of the flow sensor 10. Each of the pressure tube connectors 52 is fluidly connected to a corresponding pressure tap 44a, 44b disposed on axially opposed ends of a flow restrictor 38. As will be described in greater detail below, pressure differential is measured across the pressure taps 44a, 44b of the flow restrictor 38.

The pressure measurements may be fed to a pressure transducer or other pressure conversion device by means of a pair of pressure tubes extending from the fittings 54. As is well known in the art, pressure transducers can be used to determine flow rate such as by using a lookup table. Flow rate information is used to generate an electrical signal representative of the pressure measurements at the pressure taps 44a, 44b. The electrical signals may be used to cycle or activate a mechanical ventilator 12 (not shown) and an exhalation valve/PEEP valve (not shown) according to patient-initiated inspiration and exhalation at the appropriate time.

The flow sensor 10 illustrated in FIGS. 1 through 10 has a ventilator end 24 and a patient end 26. The ventilator end 24 is fluidly connected to the ventilator 12 such as via a wye fitting (not shown). The flow sensor 10 may be integrated into the wye fitting or may be provided as a separate component which is fluidly connected to the wye fitting such as on an end thereof adjacent the patient. In this regard, the flow sensor 10 may be adapted for use with the mechanical ventilation system disclosed in U.S. Pat. No. 6,102,038 issued to DeVries et al., the entire contents of which is expressly incorporated by reference hereinto. The patient end 26 of the flow sensor 10 may be fluidly connected to the patient airway such as via the adapter 70/endotracheal tube 16 illustrated in FIGS. 1 and 2. Optionally, the flow sensor 10 may be integrated into the wye fitting such as the type disclosed in the DeVries reference. The flow sensor 10 and wye fitting may be formed as a unitary structure such as, for example, by injection molding.

The flow sensor 10 is generally configured as an elongated, hollow tubular member 18 having a bore 20 extending therethrough. The bore 20 includes an interior surface 28 and defines a longitudinal or central axis 22 extending through the bore 20. A baffle 56 may be disposed within the bore 20 at the ventilator end 24. The baffle 56 generally comprises a plurality of vanes 58 which are sized and configured to reduce pneumatic noise by minimizing or straightening non-axial flow into the ventilator end 24. As was earlier mentioned, the mechanical ventilator 12 may be configured to produce a bias flow which passes from the mechanical ventilator 12 into the wye fitting making a significant turn in the wye fitting.

As was earlier mentioned, the bias flow may be a spiral-shaped, twisting flow entering the ventilator end 24 in a non-axial direction. Without the baffle 56, the non-axial bias flow would impinge upon the ventilator end 24 pressure tap 44a in a cross flow direction resulting in erroneous differential pressure measurements. Importantly, the baffle 56 is specifically sized and configured to reduce or minimize angular or vortex flow entering the bore 20 at the ventilator end 24 such that the flow is axially aligned upon reaching the flow restrictor 38.

Figure 3:
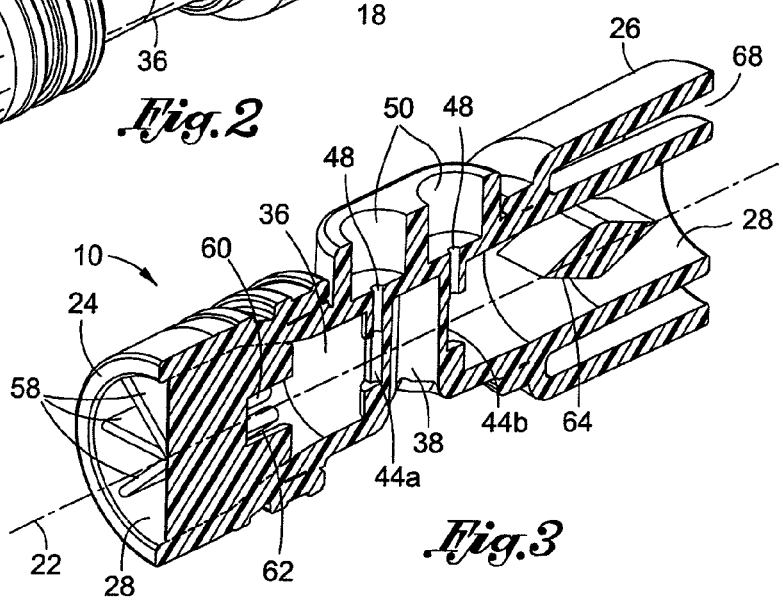
FIG. 3 is a longitudinal sectional view of the flow sensor illustrating a baffle disposed at a ventilator end, a flow obstruction disposed at the patient end and a flow restrictor interposed between the baffle and the flow obstruction.
Figure 9:
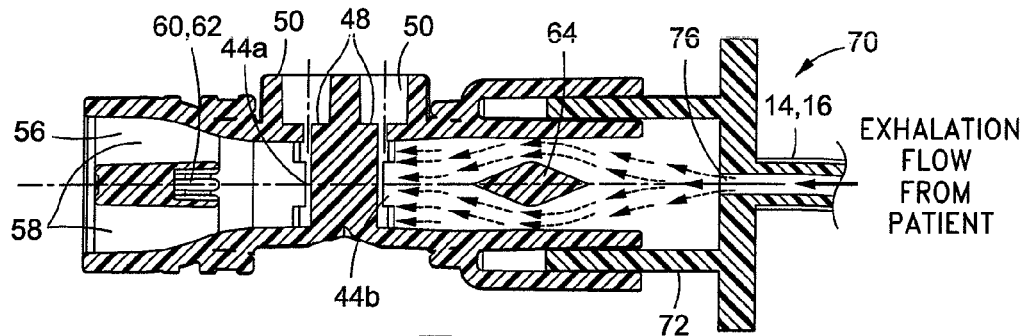
FIG. 9 is a longitudinal sectional view of the flow sensor illustrating the flow obstruction at the patient end.

Referring to FIG. 3, the flow obstruction 64 can be seen disposed within the bore 20 adjacent the patient end 26 of the flow restrictor 38. As was earlier mentioned, the flow obstruction 64 is preferably provided with an aerodynamic cross sectional shape. The flow obstruction 64 is also preferably positioned to be in general alignment with the pressure jet discharging from the endotracheal tube 16 as best seen in FIG. 9. The flow obstruction 64 promotes uniform velocity across the patient end 26 pressure tap 44b in order to allow accurate pressure measurement of exhalation flow from the patient.

Referring to FIGS. 4a to 8, the bore 20 of the tubular member 18 may include a throat section 36 between the ventilator end 24 and the patient end 26. The throat section 36 can be seen as having a reduced cross sectional area relative to the cross sectional area at the ventilator end 24 and/or patient end 26. It should be noted herein that although the tubular member 18 is shown and described as being a generally cylindrical or hollow tubular member 18, the tubular member 18 may be provided in a variety of alternative shapes and configurations. For example, the bore 20 may be provided with a cross sectional shape that is oval or square or another shape. However, the circular cross sectional shape of the bore 20 is believed to provide favorable flow characteristics through the flow sensor and enhance the measurement of pressure at the flow restrictor 38.

The flow restrictor 38 is diametrically disposed within and bisects the throat section 36. In this regard, the flow restrictor 38 is mounted transversely relative to the central axis 22. The flow restrictor 38 is preferably configured to minimize the generation of turbulence at a downstream side of the flow restrictor 38. As may be appreciated, reference to upstream and downstream ends of the flow restrictor 38 is dependent upon the direction of flow. For example, for flow entering the ventilator end 24, the upstream side is closest to the ventilator end 24 while the downstream side of the flow restrictor 38 is closest to the patient end 26.

Conversely, for flow entering the patient end 26 such as from the endotracheal tube 16, the upstream end of the flow restrictor 38 is disposed adjacent the patient end 26 while the downstream end of the flow restrictor 38 is disposed adjacent the ventilator end 24. Advantageously, the flow sensor 10 is operative to measure flow in two directions (i.e., bi-directional). The upstream end of the flow restrictor 38 is the high pressure end while the downstream end is the low pressure end. The difference in pressure between the upstream and downstream ends may be correlated to flow rate based on the known relationship between the square of flow and differential pressure or it can be empirically derived.

Figure 4A:
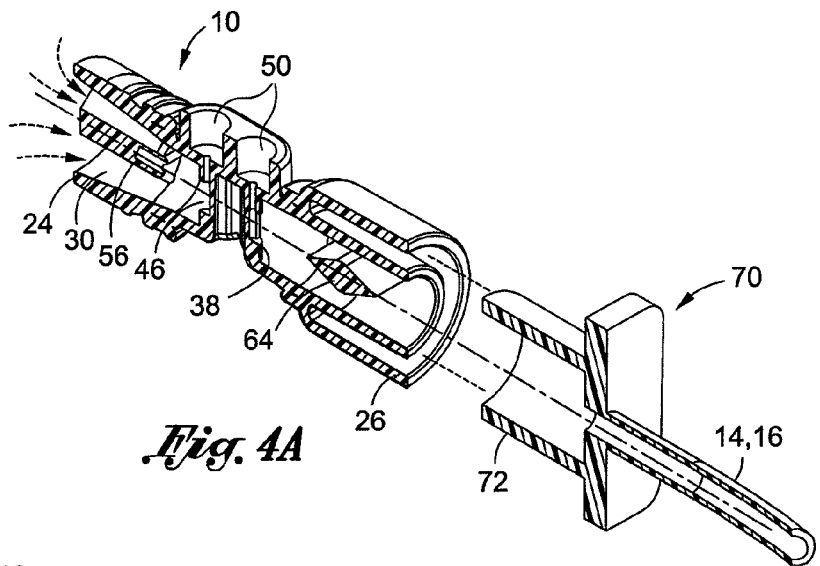
FIG. 4a is a longitudinal sectional view of the flow sensor and adapter illustrating the interconnectivity therebetween.
Figure 4B:
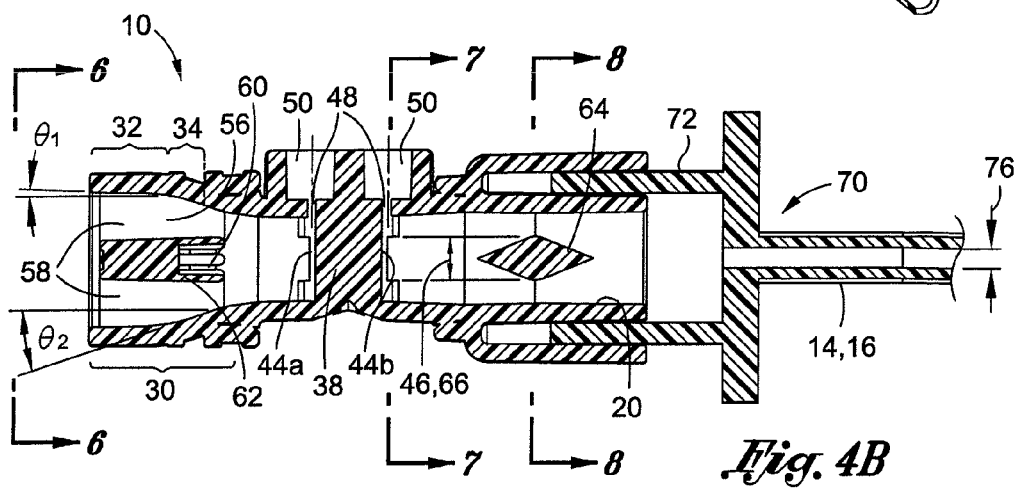
FIG. 4b is a sectional side view of the flow sensor illustrating a taper section formed in the ventilator end and illustrating the relationship between the flow obstruction and the flow restrictor.
Figure 6:
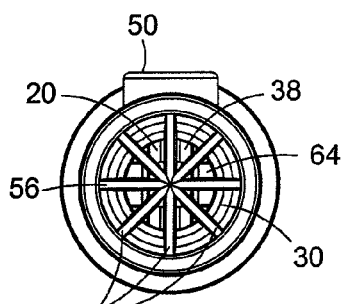
FIG. 6 is an end view of the flow sensor at the ventilator end illustrating a plurality of angularly spaced vanes comprising the baffle.
Figure 7:
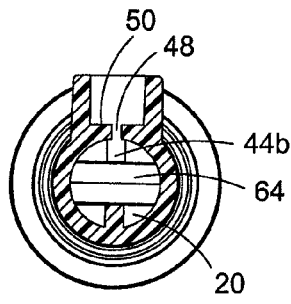
FIG. 7 is an axial cross sectional view of the flow sensor taken along lines 7-7 of FIG. 4b and further illustrating a pressure tap of the flow restrictor.

Referring to FIGS. 4a and 4b, the flow restrictor 38 includes a pair of pressure taps 44a, 44b on opposed ends of the flow restrictor 38. Each pressure tap 44a, 44b is defined as a generally open orifice or groove formed along axially opposed ends of the flow restrictor 38. The pressure taps 44a, 44b are fluidly connected by a corresponding pair of fluid passageways 48 to a pair of exterior pressure ports 50 on an outer wall of the tubular member 18. As can be seen in FIG. 7, the fluid passageways 48 extends upwardly from the pressure taps 44a, 44b to the pressure ports 50 wherein a fittings 54 fluidly communicate the pressure at the pressure taps 44a, 44b to the pressure transducer. As best seen in FIG. 4b, each of the pressure taps 44a, 44b defines a tap height 46 which is preferably symmetrically disposed about the central axis 22 of the bore 20 and which is also preferably equal to or less than an obstruction height 66 of the flow obstruction 64.

Figure 5:
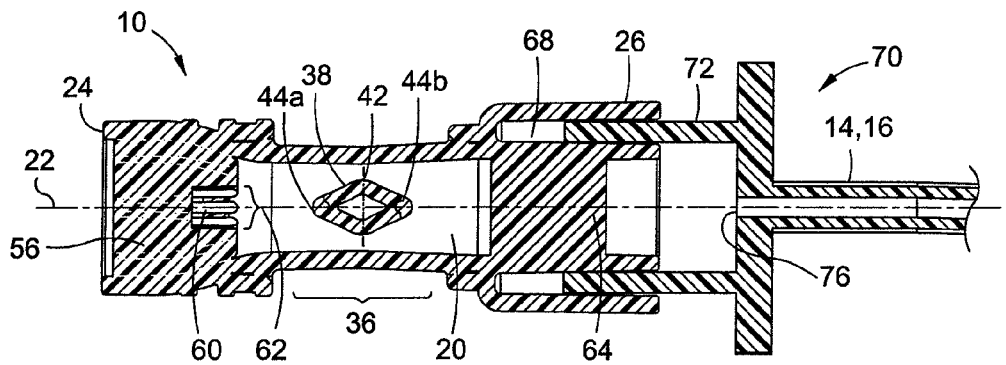
FIG. 5 is a longitudinal sectional top view of the flow sensor illustrating the cross section of the flow obstruction and the axial cross section of the flow restrictor.

Referring briefly back to FIG. 5, the flow restrictor 38 preferably has an aerodynamic shape in order to minimize disruptions in the flow. For example, the flow restrictor 38 is preferably provided with an oblong shape such as a diamond, oval or other suitable cross sectional shape to minimize the generation of turbulence in the flow which may reduce the accuracy of pressure measurements as well as increase the resistance to flow.

Referring to FIGS. 2, 3, 4b and 6, shown is the baffle 56 disposed within the bore 20 at the ventilator end 24. As can be seen, the baffle 56 comprises a plurality of vanes 58 which extend radially outwardly from the central axis 22. Each of the vanes 58 may be generally axially aligned with the central axis 22. The vanes 58 extend radially outwardly from the central axis 22 to the interior surface 28 of the bore 20. The baffle 56 is preferably sized and configured to minimize non-axial flow at the pressure taps 44a, 44b. In this regard, the baffle 56 straightens angular or vortex flow entering the flow sensor 10.

The baffle 56 is specifically adapted to minimize cross flow at the flow restrictor 38 which can otherwise result in erroneous pressure differential measurements. Although eight vanes 58 are shown, the baffle 56 may comprise any number of vanes 58. For example, the baffle 56 may comprise a pair of diametrically opposed vanes 58 which collectively bisect the bore 20 at the ventilator end 24. Alternatively, the baffle 56 may comprise four of the vanes 58 which are preferably oriented orthogonally (i.e., 90°) relative to one another. Most preferably, the baffle 56 comprises eight of the vanes 58 as illustrated in the figures wherein each of the vanes 58 is equally angularly spaced relative to one another.

Referring particularly to FIG. 4b, the bore 20 may include a taper section 30 located adjacent the baffle 56 wherein the bore 20 tapers radially inwardly along a direction from the ventilator end 24 toward the throat section 36. In this regard, flow entering the ventilator end 24 is constricted as it flows toward the throat section 36. The taper section 30 may be a single taper section disposed between the extreme ends of the bore 20 or the taper section 30 may be comprised of progressively steeper first and second tapers 32, 34.

In one embodiment best seen in FIG. 4b, the first taper 32 may have a half angle (i.e., relative to the central axis 22) of up to approximately 2° as indicated by the reference character $\theta_1$. The second taper 34 is disposed axially inwardly from the first taper 32 and preferably has a half angle, indicated by the reference character $\theta_2$, of between approximately 12° and approximately 16° (relative to the central axis 22). Transitions between the first and second tapers 32, 34 and the throat section 36 are preferably with a smooth radius in order to avoid disruption in the flow which may generate noise-producing eddies or turbulence.

Each one of the vanes 58 preferably includes a notch 60 formed on a radially inward side (i.e., along the central axis 22) and opposite the ventilator end 24. The formation of the notch 60 may be generally located in the area of the second taper 34 of the bore 20 and allows localized high pressure in any one of the vane 58 passages to be relieved by discharging of any differential (i.e., vane-to-vane) pressure. In this regard, the pressure relief 62 reduces the amount of pneumatic noise and cross flow in the area of the pressure taps 44a, 44b to improve pressure measurement accuracy.

Referring still to FIG. 4b, shown is the flow obstruction 64 interposed between the patient end 26 and the flow restrictor 38. The flow obstruction 64 is mounted transverse to the central axis 22 but is oriented perpendicularly relative to the flow restrictor 38 when viewed from an axial direction. The flow obstruction 64 bisects the bore 20 and preferably has an aerodynamic cross sectional shape in a transverse direction. The shape preferably has an aspect ratio aligned with the central axis 22. The aerodynamic cross sectional shape may be a diamond shape as illustrated in the figures or any other alternative shape. For example, the flow obstruction 64 may be provided with a teardrop axial cross section wherein the leading edge of the teardrop faces the patient end 26 and the trailing edge of the teardrop faces the ventilator end 24.

It is further contemplated that when viewed in an axial direction, the flow obstruction 64 and flow restrictor 38 are aligned with one another. However, a more preferable relationship is that which is illustrated in the figures wherein the flow obstruction 64 is oriented orthogonally or perpendicularly relative to the flow restrictor 38 when viewed in an axial direction. Such an arrangement has been proven to promote better uniformity in the flow velocity across the cross section of the bore 20.

Referring particularly to FIGS. 4b and 9, the flow obstruction 64 defines an obstruction height 66. The obstruction height 66 is preferably at least equivalent to the tap height 46 of each one of the pressure taps 44a, 44b such that the pressure jet discharged from the endotracheal tube 16 as shown in FIG. 9 is dispersed into a more uniform velocity profile rather than a direct high velocity pressure jet impinging on the pressure taps 44a, 44b. As was earlier mentioned, the high velocity pressure jet at the pressure taps 44a, 44b would otherwise result in inaccurate flow measurements. It is also contemplated that the obstruction height 66 may be greater than the tap heights 46 of the pressure taps 44a, 44b.

Figure 8:
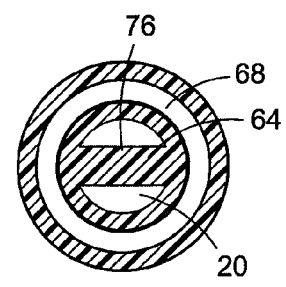
FIG. 8 is an axial cross sectional view of the flow sensor taken along lines 8-8 of FIG. 4b and illustrating an outer circumferential flange at the patient end.

Referring briefly to FIG. 8, shown is an axial cross sectional view of the flow sensor 10 at the patient end 26 and which illustrates an annular groove 68 formed at the patient end 26 for engagement to a standard-sized adapter 70. As was earlier mentioned, such adapter 70 may be a commonly-available airway adapter 70 used for attaching various size patient tubes (i.e., endotracheal tubes 16) to the flow sensor 10. As can be seen in FIG. 4b, the adapter 70 includes a cylindrical extension 72 which is sized and configured to frictionally engage the annular groove 68.

Figure 10:
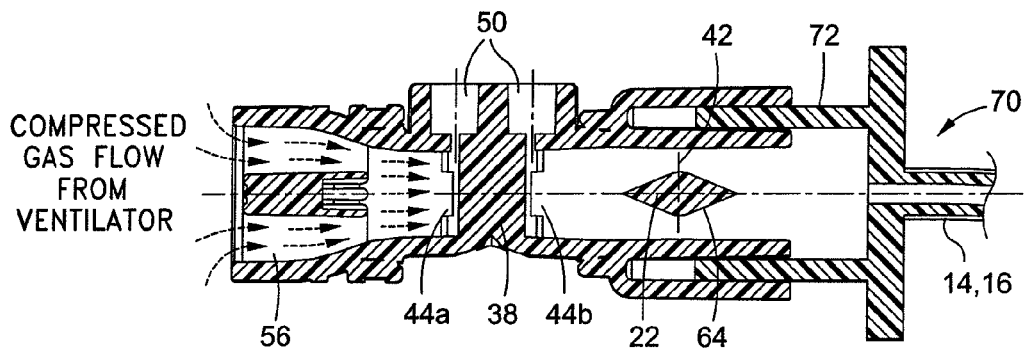
FIG. 10 is a longitudinal sectional view of the flow sensor illustrating a spiral direction of the flow entering the ventilator end and the straightening effects of the baffle.

In operation, during a patient-inspired inhalation phase, flow (e.g., such as bias flow) from the mechanical ventilator 12 enters the ventilator end 24 as best seen in FIG. 10. The bias flow may include pneumatic noise such as vibrations, turbulence or asymmetric flow induced by the curved flow path from the mechanical ventilator into the wye fitting. Flow from the mechanical ventilator 12 passes through the vanes 58 which extend radially outwardly from the central axis 22.

As was earlier mentioned, the vanes 58 are preferably sized and configured to straighten non-axial flow at the pressure taps 44a, 44b in order to ensure accurate pressure measurement. The pressure relief 62 collectively formed by the notches 60 in the vanes 58 is specifically sized and configured to discharge or equalize any differential pressure between the vanes 58 prior to the flow reaching the flow restrictor 38. The flow then passes to the patient via the endotracheal tube 16 such as that which is illustrated in FIG. 4a.

During the exhalation phase, expired gas is discharged as a high pressure jet from the endotracheal tube 16 as shown in FIG. 9. The high pressure jet enters the flow sensor 10 at the patient end 26 whereupon the flow obstruction 64 causes dispersion of the flow. The flow obstruction 64 preferably has a height which is at least equal to the tap height 46 of each of the pressure taps 44a, 44b on the flow restrictor 38 to minimize or eliminate direct impingement of the pressure jet from the endotracheal tube 16 upon the pressure taps 44a, 44b. This geometric relationship between the obstruction height 66 and the tap height 46 prevents an artificially high flow rate measurement.

Instead, the flow obstruction 64 promotes a uniform velocity profile across the bore 20 at the pressure taps 44a, 44b for the flow passing from the patient end 26 and exiting the ventilation end. Advantageously, the flow obstruction 64 allows for a flow sensor 10 configuration which reduces deadspace at the patient interface. As was previously mentioned, excessive deadspace is especially undesirable in mechanical ventilation.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A bi-directional flow sensor for sensing pressure of a flow passing therethrough, the flow sensor comprising:
    a hollow tubular member having a ventilator end and a patient end and defining a bore with a central axis, the bore including a throat section disposed between the ventilator end and patient end;
    a flow restrictor bisecting the throat section and including a pair of pressure taps each defining a tap height; and
    a flow obstruction disposed between the flow restrictor and the patient end, bisecting the bore along a transverse cross section, and being configured to promote uniform velocity across the bore at the pressure taps, wherein the flow obstruction comprises a first aerodynamic end extending transversely across the bore and disposed toward the patient end, and a second aerodynamic end extending transversely across the bore and disposed toward the ventilator end, and wherein each tap height of said tap heights is one of equal to or less than a height of said flow obstruction,
    wherein the flow obstruction is oriented perpendicularly relative to the flow restrictor when viewed in an axial direction with respect to the central axis.

2. The flow sensor of claim 1 wherein the tap height of each one of the pressure taps is symmetrical about the central axis.

3. The flow sensor of claim 1 wherein the first aerodynamic end comprises a first pointed end that points toward the patient.

4. The flow sensor of claim 3, wherein the flow obstruction has a diamond-shaped axial cross section.

5. The flow sensor of claim 1 wherein the flow obstruction has a teardrop-shaped axial cross section.

6. The flow sensor of claim 1 wherein the flow restrictor has an oblong-shaped axial cross section.

7. The flow sensor of claim 6 wherein the flow restrictor has a diamond-shaped axial cross section.

8. The flow sensor of claim 1 wherein the flow sensor is integrated into a wye fitting.

9. A bi-directional flow sensor for sensing pressure of a flow passing therethrough, the flow sensor comprising:
    a hollow tubular member having a ventilator end and a patient end and defining a bore with a central axis, the bore including a throat section disposed between the ventilator end and patient end;
    a flow restrictor bisecting the throat section and including a pair of pressure taps each defining a tap height;
    a flow obstruction disposed at the patient end and bisecting the bore along a transverse cross section in a manner perpendicular to the flow restrictor when viewed in an axial direction with respect to the central axis; and
    a baffle disposed within the bore at the ventilator end and comprising a plurality of vanes, the baffle being sized and configured to minimize non-axial flow at the pressure taps.

10. The flow sensor of claim 9 wherein the vanes are radially oriented.

11. The flow sensor of claim 10 wherein the baffle comprises up to eight of the vanes positioned equiangularly relative to one another.

12. The flow sensor of claim 9 wherein each one of the vanes includes a notch on a radially inward side thereof such that the notches collectively define a pressure relief by discharging vane to vane pressure.

13. The flow sensor of claim 9 wherein the bore includes a taper section located adjacent the baffle and tapering radially inwardly along a direction from the ventilator end toward the patient end.

14. The flow sensor of claim 9 wherein the tap height of each one of the pressure taps is symmetrical about the central axis.

15. The flow sensor of claim 9 adapted for use with a mechanical ventilator and being configured such that pneumatic noise is maintained at less than about 0.1 liters per minute (LPM).

16. The flow sensor of claim 9 wherein the flow sensor is integrated into a wye fitting.

17. The flow sensor of claim 9 wherein the flow obstruction further comprises a first aerodynamic end extending transversely across the bore and disposed toward the patient end, and a second aerodynamic end extending transversely across the bore and disposed toward the ventilator end.

18. The flow sensor of claim 17 wherein the first aerodynamic end disposed toward the patient end comprises a first pointed end that points toward the patient end, and the second aerodynamic end comprises a second pointed end that points toward the ventilator end.

* * * * *